United States Patent
Coakley et al.

(10) Patent No.: US 7,608,440 B2
(45) Date of Patent: Oct. 27, 2009

(54) APPARATUS FOR ULTRASONIC MICROBIAL DISRUPTION

(75) Inventors: William Terence Coakley, Cardiff (GB); Kathryn Amelia Jane Borthwick, Cardiff (GB); Martin Bernard McDonnell, Salisbury (GB); Tracey Elizabeth Love, Salisbury (GB)

(73) Assignee: The Secretary of State for Defence in Her Britannic Majesty's Government of the United Kingdom of Great Britain and Northern Ireland (GB)

( * ) Notice: Subject to any disclaimer, the term of this patent is extended or adjusted under 35 U.S.C. 154(b) by 416 days.

(21) Appl. No.: 10/571,029

(22) PCT Filed: Sep. 7, 2004

(86) PCT No.: PCT/GB2004/003827

§ 371 (c)(1),
(2), (4) Date: Mar. 8, 2006

(87) PCT Pub. No.: WO2005/023978

PCT Pub. Date: Mar. 17, 2005

(65) Prior Publication Data

US 2006/0252141 A1      Nov. 9, 2006

(30) Foreign Application Priority Data

Sep. 8, 2003    (GB) ................................ 0320954.1

(51) Int. Cl.
*C12N 13/00*    (2006.01)
(52) U.S. Cl. ............... 435/173.7; 435/173.1; 435/173.4
(58) Field of Classification Search ............. 435/173.1, 435/173.4, 173.7
See application file for complete search history.

(56) References Cited

U.S. PATENT DOCUMENTS

| | | | | |
|---|---|---|---|---|
| 3,561,444 A | * | 2/1971 | Boucher | ................ 128/200.16 |
| 6,071,480 A | * | 6/2000 | Halaka | ....................... 422/128 |
| 6,492,762 B1 | * | 12/2002 | Pant et al. | .................... 310/334 |
| 6,506,584 B1 | | 1/2003 | Chandler et al. | |

FOREIGN PATENT DOCUMENTS

| | | |
|---|---|---|
| EP | 0337690 | 10/1989 |
| WO | WO 03/101609 | 12/2003 |

* cited by examiner

*Primary Examiner*—Cecilia Tsang
*Assistant Examiner*—Susan E. Fernandez
(74) *Attorney, Agent, or Firm*—Dean W. Russell; Kilpatrick Stockton LLP

(57) ABSTRACT

Apparatus for microbial disruption, comprises a cylindrical transducer having a beat conducting, solid transmission layer disposed along at least a part of the inner longitudinal surface thereof, said transmission layer or said transducer and transmission layer defining a channel for receipt of a liquid sample, and means capable of delivering an alternating potential to said transducer at a frequency and voltage exciting resonance and inducing cavitation in said liquid sample.

21 Claims, 3 Drawing Sheets

APPARATUS FOR ULTRASONIC MICROBIAL DISRUPTION

CROSS REFERENCE TO RELATED APPLICATIONS

This application is the U.S. national phase of International Application No. PCT/GB2004/003827 filed on Sep. 7, 2004 published in English on Mar. 17, 2005 as International Publication No. WO 2005/023978 A1, which application claims priority to Great Britain Application No. 0320954.1 filed on Sep. 8, 2003, the contents of which are incorporated by reference herein.

The present invention is generally concerned with apparatus for the disruption of microbes by exposure to radially focused ultrasound. The present invention is particularly, although not exclusively, directed to compact apparatus suitable for use in aiding detection and analysis of pathogenic bacteria.

Commercially available devices for the disruption of microorganisms by ultrasonic cavitation typically comprise applicators resonant at 20 kHz. The half-wavelength (maximal transmission) probes are often about 15 cm in length and are, therefore, bulky and inconvenient to use where small sample volumes of pathogenic bacteria are to be disrupted. Further, because the probes must be immersed in a liquid sample of these bacteria there is an inherent risk of formation of a hazardous aerosol.

More compact cell disruption devices that operate at higher frequencies are known. For example, a bacterial cell disrupter using ultrasonic energy transmitted from a horn through a flexible, thin film interface with the liquid (Taylor, M. T. et al., Anal. Chem., 2001, 73, 492-496) operates at 40 kHz. In addition, a cell disrupter comprising a 160° segment of a tubular transducer of thickness 1 MHz that focuses sound through water to a spore suspension in a narrow plastic tube (Chandler et al., ibid., 2001, 73, 3784-3789) is known.

However, whilst each of these devices effectively disrupt bacteria through high sound pressures, they generate a significant amount of heat leading to a substantial rise in the temperature of the sample to as much as 50 to 90° C. Such high temperatures are tolerable where the purpose of the disruption is to extract DNA for PCR analysis but are deleterious to the antigenicity of, for example, a protein antigen.

The disruption of bacteria facilitating immunoassay of protein and cell wall fragments does, however, offer a significant advantage in that a large number of potential fragments are potentially detectable.

The present invention, therefore, generally seeks to provide a compact apparatus enabling rapid disruption of microbes, for example bacteria, in a liquid sample thereof with minimal temperature rise.

Accordingly, the present invention provides apparatus for ultrasonic microbial disruption, comprising a cylindrical transducer having a heat-conducting, solid transmission layer disposed along at least a part of the inner longitudinal surface thereof, said transmission layer or said transducer and transmission layer defining a channel for receipt of a liquid sample, and means capable of delivering an alternating potential to said transducer at a frequency and voltage exciting resonance and inducing cavitation in said liquid sample.

As used herein, the term "liquid sample" refers to a suspension of a microbe, for example, bacteria or spores, in a liquid, normally water.

It will be understood that the drive frequency necessary to excite one or more resonance depends on the material and thickness of the transducer wall and the transmission layer as well as the diameter or width of the channel (or thickness of the sample layer).

The transducer wall will normally have thickness about an odd integral multiple of the half-wavelength of sound therein. The thickness is otherwise not limited except by the requirement for resonance and compact apparatus.

Preferably, the transmission layer has thickness about an integral multiple (even or odd) of the half-wavelength of sound therein so as to maximise transmission of the sound wave. Most preferably, the transmission layer has thickness about a half wavelength of sound therein. The thickness is otherwise not limited except by the requirement for resonance and compact apparatus.

The width or diameter of the channel is also selected so as to enable resonance. Preferably, the width or diameter facilitates cavitation in a reasonable volume of the liquid sample whilst maintaining it in the focusing region of the transducer. Still more preferably, the width or diameter of the channel supports good heat transfer to the transmission layer from the bulk liquid sample.

The ability of the cylindrical transducer, driven in radial mode, to provide high sound pressures in its focusing region (at or adjacent the longitudinal axis) is dependent on its outer diameter. The diameter is, therefore, preferably as large as possible whilst meeting the requirement for compact apparatus—particularly where the thickness of the transmission layer is great.

The longitudinal length of the transducer is not limited according to the present invention other than a requirement for compactness. Preferably, the length provides a degree of uniformity of energy density along the channel without detriment to its impedance.

A preferred cylindrical transducer (PZT4D, 298 kHz, Vernitron, Southampton, UK) comprises a tubular piezoceramic having wall thickness about 6.5 mm, outer diameter about 63.7 mm and length about 25.6 mm.

The transmission layer may be disposed along a portion or segment of the inner surface of the cylindrical transducer. In particular, the transmission layer may comprise a half-cylinder disposed across half of this inner surface. In a preferred embodiment however, the transmission layer comprises a whole cylindrical tube. The preferred embodiment is of maximal efficiency compared with a liquid or part liquid transmission layer in that cavitation therein is avoided.

It will be apparent that the transmission layer alone or the transducer and the transmission layer together define a channel. In a preferred embodiment the channel is defined by the transmission layer and is of circular cross-section and concentric with the longitudinal axis of the cylindrical transducer. In this embodiment good overlap of an introduced liquid sample with the focusing region is obtained. However, other arrangements in which the channel is offset from the longitudinal axis of the cylindrical transducer and/or non-circular are envisaged.

The transmission layer may comprise any suitable heat conducting material. The material conducts heat away from the sample so controlling the rapid heating of the sample at such high pressures. Preferably, the longitudinal length of the transmission layer exceeds that of the transducer so as to ensure that heat is conducted well away from the focusing region. Suitable transmitting and conducting materials comprise metal or metal alloys such as steel.

A preferred transmission layer comprises a steel cylinder having outer diameter about 50.5 mm, inner diameter about 3.8 mm diameter and length about 31.9 mm. The wall thickness of the transmission layer is about 20.5 mm (half wavelength).

The transmission layer will normally be secured to the inner surface of the cylindrical transducer by a suitable adhesive such as an epoxy resin. In particular, the preferred steel cylinder may be coated with a silver loaded conductive epoxy resin and the cylindrical transducer gently pushed on.

The preferred cylindrical transducer and preferred transmission layer provide significant cavitation in a liquid sample at three frequencies as determined by stereoscopic observation. The lowest frequency 266 kHz occurs close to the prediction of a resonance frequency according to a one dimensional transfer matrix, multilayer resonance model. Significant cavitation also occurs at 297 kHz and 314 kHz, coincide with measured electrical resonances and are close to the nominal 298 kHz thickness resonance of the transducer.

A preferred drive frequency is 266 kHz although comparable bacterial cell disruption is obtained at 297 kHz.

In one embodiment the apparatus further comprise means delivering sample flow through the channel such as a tube and pump arrangement. In an alternative embodiment the apparatus is adapted, for example by closure means or valve means, so as to maintain the liquid sample in the channel and enable batch processing.

In other embodiments the apparatus further comprise cooling means facilitating the removal of heat from the liquid sample. The cooling means may, for example, comprise a lattice heat sink coupled to the transmission layer by a suitable grease and one or more blowers.

In one embodiment, suitable for batch processing, in which the cylindrical transducer is vertical in use, a first blower blows air across the apparatus and through a heat sink disposed in thermal contact with the steel cylinder. A second blower blows air downwards from above the apparatus.

The present invention also provides a method for microbial disruption comprising i) introducing a liquid sample to apparatus comprising a cylindrical transducer having a heat-conducting, solid transmission layer along at least a part of the inner longitudinal surface thereof, said transmission layer or said transducer and transmission layer defining a channel receiving said sample and ii) applying an alternating potential to said transducer at a frequency and voltage exciting resonance and inducing cavitation in said liquid sample.

The method may be performed with any of the previously described embodiments of the apparatus of the present invention. The frequency of the alternating potential is, in practice, determined by a computer-controlled sweep at particular potentials and optical/aural observation of cavitation. Suitable applied potentials for obtaining strong resonance range from 30 to 100 $V_{rms}$.

In a preferred embodiment, the method is performed with a drive frequency ranging from 264 to 314 kHz, optimally 266 kHz, at about 80 $V_{rms}$.

The method of the present invention may be performed as a batch or continuous process. For a batch process, the apparatus is vertically arranged with the sample liquid retained in the channel by, for example, a thin plastic film and a grommit. The liquid sample is then sonicated at the determined optimal frequency during one or more time periods. The number and extent of the time periods are selected so as to minimise heating of the liquid sample and maximise cell disruption.

A continuous process is suitable where the extent of cell disruption is high during a short time period. For the preferred apparatus, flow rates of about 1 ml/min of a liquid sample containing bacterial spores are envisaged. The continuous process, therefore, offers the potential of integration of cell disruption to detection technologies employing flow techniques.

The present invention will now be described by way of example only with reference to the following Examples and drawings in which FIG. 1 is a front elevation view of the apparatus according to the preferred embodiment of the present invention;

FIG. 2 *a*) and *b*) are respectively an end and section view of the apparatus of FIG. 1;

Figure 1:
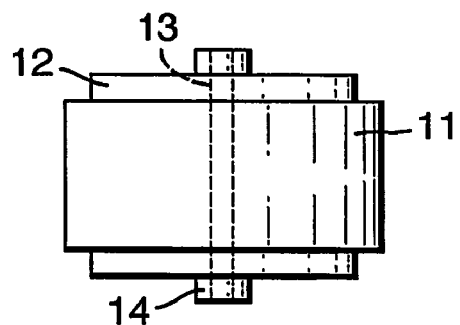
Figure 5A:
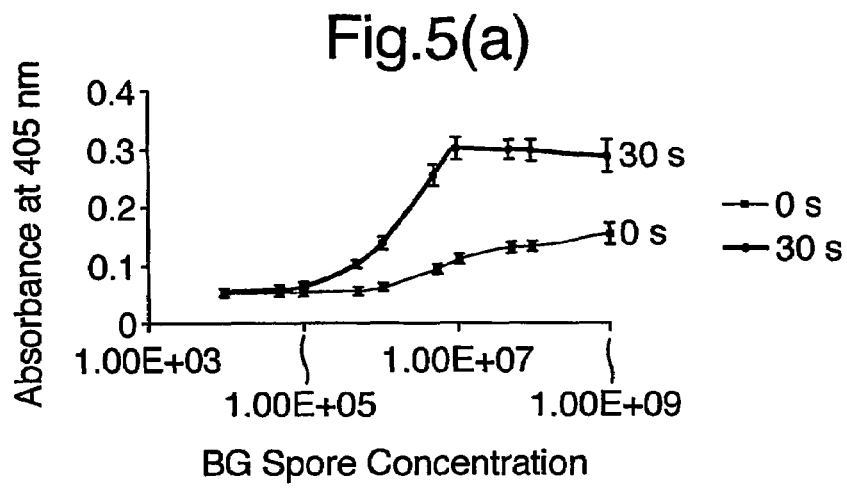
Figure 5B:
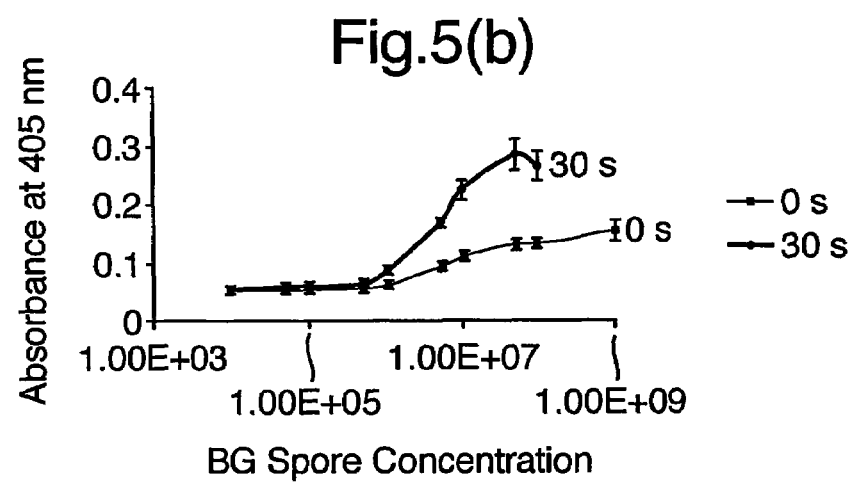
Figure 5C:
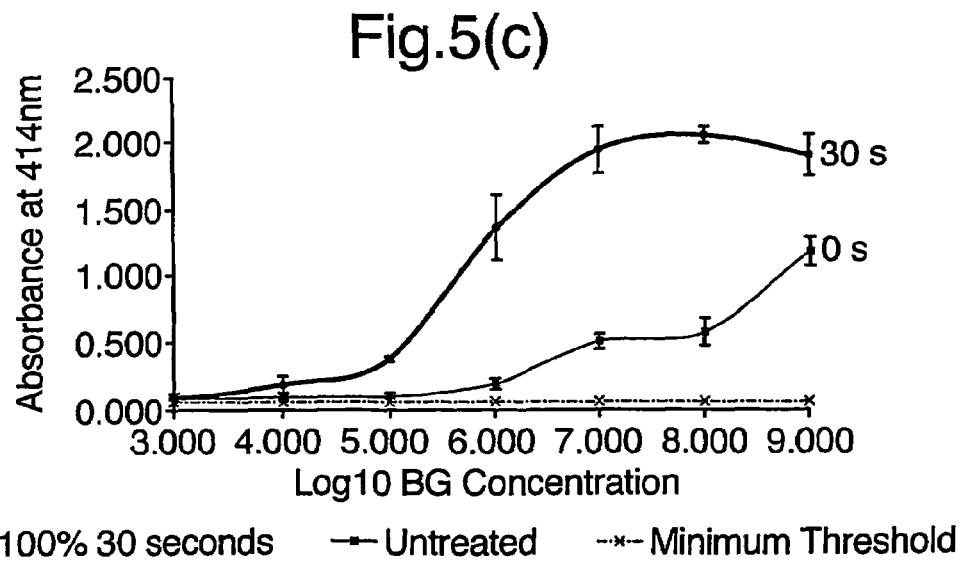

FIGS. 5 *a*) *b*) and *c*) are respectively graphs showing detection of *Bacillus subtilis* var. *niger* (BG) spore antigens as measured by adsorption spectroscopy using the apparatus of FIG. 1 and two commercially available 20 kHz ultrasonic microbial disrupters.

Figure 2A:
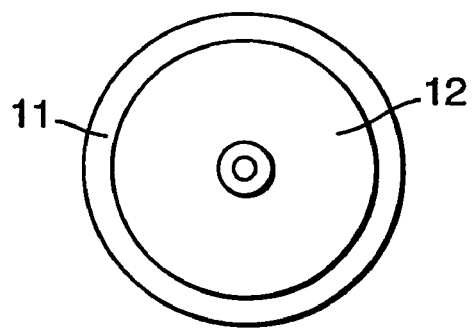
Figure 2B:
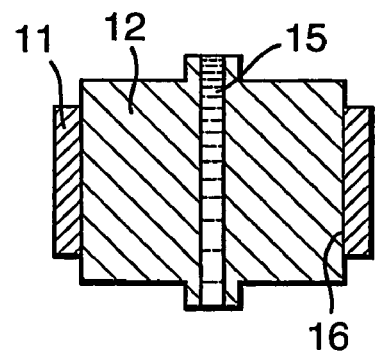

Referring now to FIGS. 1 and 2, a preferred embodiment of the present invention comprises a 25.58 mm long cylindrical ceramic transducer 11 (PZT4D, 298 kHz, Vernitron, Southampton, UK) of outer diameter 63.76 mm and wall thickness 6.52 mm. The cylindrical transducer is fitted with a 31.91 mm long steel cylinder 12 of outer diameter 50.50 mm and inner diameter 3.8. The cylinder defines a channel 13 (FIG. 1, dotted line) for the receipt of a liquid sample 15 through protruding tubular portions 14 arranged on the upper and lower surfaces of the steel cylinder.

The steel cylinder is secured to the cylindrical transducer by a silver-loaded conductive epoxy resin 16. An alternating potential source (not shown) comprising a wave generator (Agilent model HP 33120A) and an amplifier (Model 240L, ENI, Rochester, N.Y.) delivers an alternating potential ranging from about 30 to 100 $V_{rms}$ to the transducer.

Electrical impedance measurements and treatment of the cylindrical acoustic multiple layer system as a planar system (water loaded) according to a one dimensional transfer matrix resonator model (Hawkes J. J. et al., Ultrasonics, 2002, 40, 385-392) predicted frequencies at which cavitation was strong in good agreement with those found experimentally.

Figure 3:
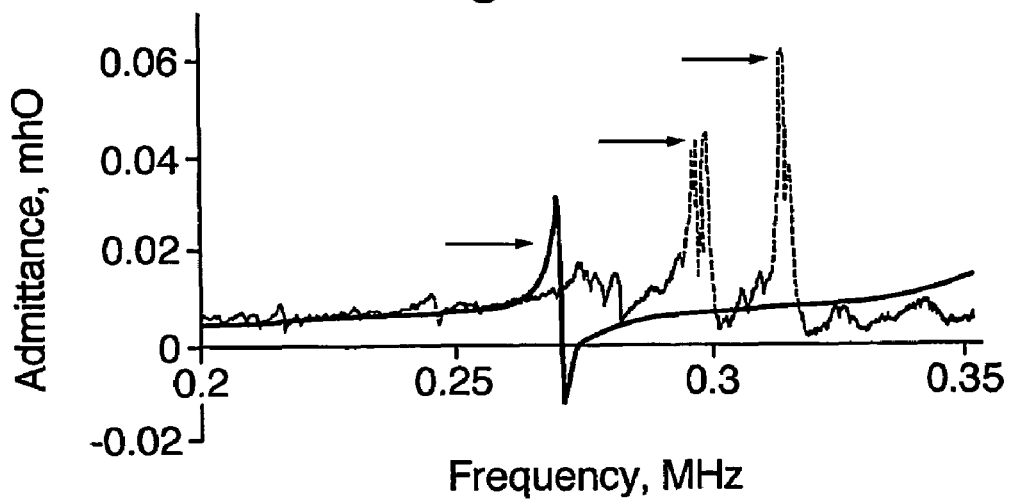
FIG. 3 is a graph showing the electric impedance plotted against frequency for the apparatus of FIG. 1.

FIG. 3 shows the frequency dependence of electric admittance measurements (dotted line) and a plane wave spectrum simulated by the model. High cavitation activity (indicated by arrows) is seen in a 4 kHz band centred at 266 kHz, at about 297 kHz and at 314 kHz.

The frequency dependence of disruption of a dilute, buffered suspension of human erythrocytes had the order 266≧297>314 kHz. The fact that the highest frequency showed least disruption may be due to less efficient matching to the amplifier for the low impedances at this frequency.

EXAMPLE 1

Batch processing of liquid samples of 0.6 ml containing a suspension of the yeast strain *Saccharomyces cerevisiae* D1 in water was performed at a drive frequency of 266 kHz at 80 $V_{rms}$.

The samples were prepared by growing the yeast in yeast extract peptone dextrose (YEPD) media (10 g yeast extract, 20 g bacteriological peptone, 20 g glucose, 0.1 g adenine and 0.1 g uracil in 1 l deionised water) in an orbital shaker (150 rpm; 25° C. for 48 h, Mk X incubator shaker, LH Engineering Co. Ltd). The cells were twice washed by centrifuging at 3000 rpm for 5 min and then re-suspended in distilled water.

The Lowry modified Folin-Ciocalteu assay was used to determine the accumulation of released protein in the sample supernatant. Microscope observation (×20 and ×40) of Methylene Blue stained cells was used to determine the number of viable cells and visualise any disrupted cell wall material.

Figure 4:
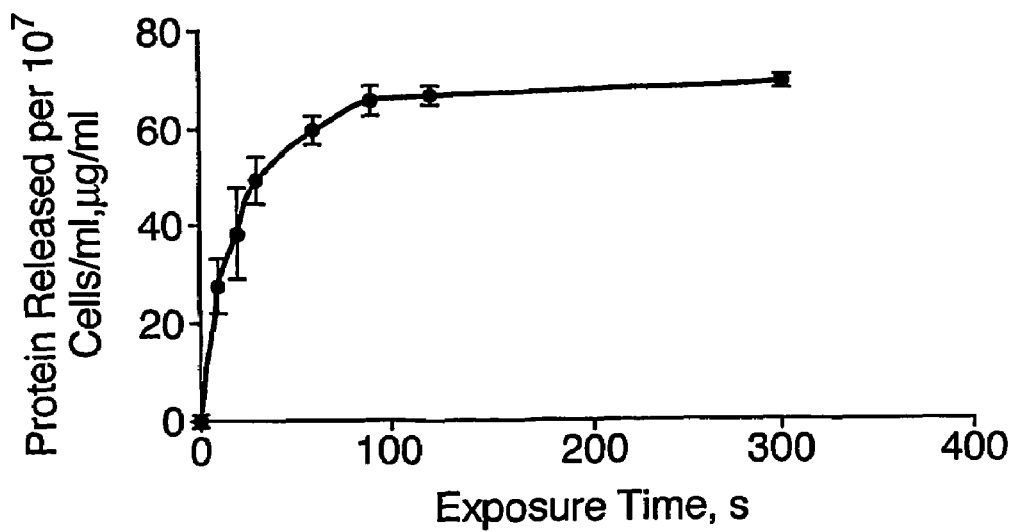
FIG. 4 is a graph showing the extent of disruption of *Saccharomyces cerevisiae* over time using the apparatus of FIG. 1.

The disruption of these yeast samples over time is shown in FIG. 4. As may be seen, protein release is rapid during the first 30 seconds of sonication. Microscope observation (×40) showed ruptured cells at 60 s. The temperature increase was measured as 13 K after 3 min. Disruption was comparable with that achieved in 2.4 ml liquid samples using a commercially available 20 kHz ultrasonic microbial disrupter.

EXAMPLE 2

A stock suspension of washed BG spores suspended in sterile distilled water was prepared ($10^{10}$ cfu/ml to $10^{11}$ cfu/ml).

Batch processing of this solution was performed on a) 0.6 ml at 266 kHz, 80 $V_{rms}$ b) 2.4 ml at 20 kHz (glass beaker over ice using a titanium probe of diameter 9.54 mm driven at 60 W; MSE Ltd, London, UK) and c) 100 ul containing 0.5 mg of 106 μM suspension of acid washed beads in smartcylcer tubes at 20 kHz using a titanium probe of diameter 6 mm driven at 100% amplitude (Cepheid, Calif., USA).

Spore antigen availability was determined at various time intervals by immunoassay based on direct ELISA utilising a polyclonal α-BG rabbit antibody raised against whole BG spores. Samples of the spores were coated to Immunlon 2, 96 well microtitre plates, diluted in bicarbonate buffer, pH 9 and incubated overnight at 4° C. The plates were washed (×3 PBS Tween 20, 0.05% and ×1 PBS) and then blocked (1% milk powder, PBS Tween 20, 0.05% over 2 h at room temperature). Addition of the antibody to a final concentration of 10 μg/ml in each well, incubation (1 h at room temperature) and washing (as previous) was followed by addition of a rabbit HRP conjugated. After incubation (1 h at room temperature) the plate was washed (×4, PBS Tween 0.05% and ×1 PBS) and ABTS development buffer added. After incubation for a period sufficient to develop colour, the absorption of the samples was measured at 405 nm wavelength.

FIG. 5 highlights the improvement in assay sensitivity to BG antigen following sonication for each apparatus a to c for 30 s (assay sensitivity was found to be greatest after 30 s suggesting that denaturation occurs with longer sonication periods).

Referring now to each graph in FIG. 5, the horizontal line drawn between the curves at $A^{405}$ 0.1 unit, suggests a fifteen-fold increase in sensitivity of the assay following sonication at 266 kHz. The improvement is at least as good as that obtained according to b although somewhat lagging to that obtained in c (twenty-fold).

Protein release was also measured from the sonicated spore samples as previously described. The pattern of release in a and b is broadly similar although a significantly higher amount of protein was released in b. It is noted that although the amount of released protein steadily increases over time the immunoassay show that the antigenicity of the samples declines. The temperature rise in the basic apparatus, the sonication process itself or the release of other spore components may contribute to this loss.

The compact apparatus according to the present invention achieves comparable results to larger, commercially available apparatus. Further, the apparatus inherently reduces deleterious heating of the sample associated with higher frequencies and radial focusing of ultrasound as compared with prior art.

The control of heating of the sample in the basic apparatus can be further improved by blower-assisted cooling as described above. In particular, the rise in temperature of a sample can be improved from 40° C. after 10 min to 11° C. after 1 h continuous sonication at 266 kHz, 80 $V_{rms}$.

The invention claimed is:

1. Apparatus for ultrasonic microbial disruption, comprising a cylindrical transducer having a heat-conducting, solid transmission layer disposed along at least a part of the inner longitudinal surface thereof, said transmission layer or said transducer and transmission layer defining a channel for receipt of a liquid sample, and means capable of delivering an alternating potential to said transducer at a frequency and voltage exciting resonance and inducing cavitation in said liquid sample.

2. The apparatus according to claim 1, in which the transmission layer has thickness about an integral multiple of the half wavelength of sound therein.

3. The apparatus according to claim 1, in which the cylindrical transducer has a wall thickness about 6.5 mm.

4. The apparatus according to claim 3, in which the cylindrical transducer has outer diameter about 63.7 mm.

5. The apparatus according to claim 1, in which the transmission layer comprises steel.

6. The apparatus according to claim 5, in which the transmission layer comprises a cylindrical tube of longitudinal length greater than the cylindrical transducer, outer diameter about 50.5 mm and wall thickness of about 20.5 mm.

7. The apparatus according to claim 6, in which the channel has width or diameter of about 3.8 mm.

8. The apparatus according to claim 1, including means for closing said channel.

9. The apparatus according to claim 1, further comprising means for delivering the sample to said channel.

10. The apparatus according to claim 1, further comprising cooling means.

11. A method for ultrasonic microbial disruption comprising i) introducing a liquid sample to an apparatus comprising a cylindrical transducer having a heat-conducting solid transmission layer along at least a part of the inner longitudinal surface thereof, said transmission layer or said transducer and transmission layer defining a channel for receiving said sample and ii) applying an alternating potential to said transducer at a frequency and voltage exciting resonance and inducing cavitation in said liquid layer.

12. The method according to claim 11, in which the transmission layer has thickness about an integral multiple of the half wavelength of sound therein.

13. The method according to claim 11, in which the cylindrical transducer has wall thickness about 6.5 mm.

14. The method according to claim 13, in which the cylindrical transducer has outer diameter about 63.7 mm.

15. The method according to claim 11, in which the transmission layer comprises steel.

16. The method according to claim 15, in which the transmission layer comprises a cylindrical tube of longitudinal length greater than the cylindrical transducer, outer diameter about 50.5 mm and wall thickness of about 20.5 mm.

17. The method according to claim 16, in which the channel has width or diameter about 3.8 mm.

18. The method according to claim 17, in which the frequency of the alternating potential ranges from 264 to 314 kHz and the magnitude of the potential is about 80 $V_{rms}$.

19. The method according to claim 11, performed as a batch process.

20. The method according to claim 11, performed as a continuous process.

21. The method according to claim 11, including cooling the apparatus.

* * * * *